United States Patent [19]

Hamburger

[11] Patent Number: 5,001,463
[45] Date of Patent: Mar. 19, 1991

[54] METHOD AND APPARATUS FOR DETECTING AIRBORNE ALLERGEN PARTICULATES

[76] Inventor: Robert N. Hamburger, 9485 La Jolla Shores Dr., La Jolla, Calif. 92037

[21] Appl. No.: 313,026

[22] Filed: Feb. 21, 1989

[51] Int. Cl.⁵ .............................................. G08B 17/10
[52] U.S. Cl. ................................. 340/627; 73/28.01; 73/28.04; 73/863.21; 73/863.23; 73/863.24; 356/438
[58] Field of Search ....................... 340/627, 628, 630; 73/28, 863.21, 863.22, 28.01, 28.02, 28.03, 28.04, 28.05, 863.23, 863.24; 137/78.5; 250/573, 576, 222.2, 574; 356/337, 339, 439, 438; 364/555

[56] References Cited

U.S. PATENT DOCUMENTS

| | | | |
|---|---|---|---|
| 2,675,697 | 4/1954 | Quynn et al. | 73/28.01 |
| 3,540,261 | 11/1970 | Scoggins | 73/863.25 |
| 3,715,911 | 2/1973 | Chuan | 73/28.03 |
| 3,845,480 | 10/1974 | Steinberg | 340/627 |
| 3,867,640 | 2/1975 | Paulsen | 250/573 |
| 4,046,593 | 9/1977 | Au et al. | 134/21 |
| 4,080,832 | 3/1978 | Moody et al. | 73/864.34 |
| 4,091,674 | 4/1978 | Amey | 73/864.34 |
| 4,117,715 | 10/1978 | Hoenig | 73/28.01 |
| 4,254,414 | 3/1981 | Street et al. | 340/627 |
| 4,350,507 | 9/1982 | Greenough et al. | 55/270 |
| 4,375,667 | 3/1983 | Buchan | 364/418 |
| 4,389,903 | 6/1983 | Bertone et al. | 73/863.03 |
| 4,475,379 | 10/1984 | Jinotti | 73/28.01 |
| 4,569,235 | 2/1986 | Conkle et al. | 73/863.03 |
| 4,583,859 | 4/1986 | Hall, Jr. | 250/573 |
| 4,617,560 | 10/1986 | Gutmann | 340/628 |
| 4,786,295 | 11/1988 | Newman et al. | 340/607 |
| 4,786,472 | 11/1988 | McConnell et al. | 73/863.21 |
| 4,839,529 | 6/1989 | Fruengel | 356/339 |

FOREIGN PATENT DOCUMENTS

2401008  8/1974  Fed. Rep. of Germany ..... 73/28.01

OTHER PUBLICATIONS

"Simslin II-Portable Airborne Dust Meas. Instrumt."; Casswell et al.; Proceeding of 4th WVA Conf. on Coal Mine Electrotech, USA (2–4 Aug. '78).

*Primary Examiner*—Joseph A. Orsino
*Assistant Examiner*—Jill Jackson
*Attorney, Agent, or Firm*—Brown, Martin, Haller & McClain

[57] ABSTRACT

An allergen detector and allergen detection method for sampling the environment where the detector is located and providing an alarm indication when allergen particulates exceed a predetermined level. The invention comprises a housing having a passageway formed therethrough with a fan disposed in the passageway that is responsive to a flow control signal for creating air flow in a first direction through the passageway. At least one filter is disposed in the passageway for removing particulates larger than allergen particulates in air flowing through the passageway in the first direction. An allergen particulate detector is disposed in the passageway downstream of the filter, with respect to air flow in the first direction, for detecting allergen particulates in the air flowing through the passageway and for providing a corresponding detection signal. A controller is disposed in the housing and coupled to the fan and the allergen detector for generating, at periodic time intervals for a predetermined time period, the flow control signal. The controller is responsive to the detection signal for generating an alarm signal when the detection signal reaches a predetermined level indicative of a condition of excessive allergen particulates present in the environment. An alarm disposed in the housing and coupled to the controller receives the alarm signal and provides an indication of the condition of excessive allergen particulates present in the environment.

20 Claims, 2 Drawing Sheets

METHOD AND APPARATUS FOR DETECTING AIRBORNE ALLERGEN PARTICULATES

BACKGROUND OF THE INVENTION

I. Field of the Invention

The present invention relates to a method and apparatus for detecting allergens in the environment. More specifically, the present invention relates to a novel and improved self-contained apparatus and method for sampling the environmental air and providing an alarm indication when allergen particulates exceed a predetermined level.

II. Background Art

Many individuals suffer from allergies or hypersensitivity to airborne particulates or particles which at times are present in the environmental air that is breathed by the individual. These particulates to which many individuals are sensitive are typically in the size range of 5-20 microns. These particles may come from various sources such as dust, pollens, mold spores, smoke, animal danders, insect body parts, foods and various other sources which produce particles in the allergen size range.

It is generally well known that it is particles of the 5-20 micron size which provoke respiratory symptoms such as asthma, coughing, sneezing rhinoconjunctivitis, as well as skin rashes and anaphylaxis. Typically larger particles do not easily pass through the nasal and pharyngeal barriers and thus generally do not produce serious symptoms. However, for those individuals who are sensitive to the allergen-sized particles, it would be desirable to be alerted to environmental conditions in which there is a presence of an excessive number of allergen particulates. Real time knowledge of the allergen particulate level in the environmental air would enable one to take measures to avoid exposure to the environmental condition, to activate filters to remove the allergens, or to seek immediate medical assistance.

Previously developed air sampling devices have operated on the basis of sampling the environment for airborne particulates for later analysis. No such device is known which is capable of providing a real time detection and warning to an individual of the condition of excess particulates, especially allergen particulates, in the environmental air. It is therefore most desirable to have a device that is capable of providing almost instantaneous warning of allergy provoking environmental conditions so that the individual may take steps to avoid further exposure.

It is therefore an object of the present invention to provide a new and improved air sampling device and method for detecting the presence of an excessive number of allergen particulates and providing concurrently therewith an alarm condition indication when the allergen particulates exceed a predetermined level.

It is yet a further object of the invention to provide a self-contained, real-time allergen detection device capable of providing a warning to sensitive individuals of the presence of allergen particles in respired air.

It is yet a further object of the present invention to provide along with a real time warning of the presence of excessive of airborne allergen particles, means by which the particles may be trapped for later analysis.

SUMMARY OF THE INVENTION

The present invention relates to an allergen detector for sampling the environment where located and providing an alarm indication when allergen particles or particulates exceed a predetermined level. The detector includes a housing having a passageway formed therethrough with flow means disposed in the passageway responsive to a flow control signal for creating air flow in a first direction through the passageway. A filter means is disposed in the passageway for removing particulates larger than allergen particulates in air flowing through the passageway in the first direction. An allergen particulate detector means is disposed in the passageway downstream of the filter means with respect to the first direction of air flow for detecting allergen particulates in air flowing through the passageway, and for providing a corresponding detection signal. Controller means is disposed in the housing and coupled to the flow means and the allergen particulate detector means for, at periodic time intervals, generating for a predetermined time, the flow control signal. The controller means is responsive to the detection signal for generating an alarm signal when the particulate signal reaches a predetermined level indicative of a condition of excessive allergen particulates present in the environment. An alarm indicator means disposed in the housing and coupled to the controller means receives the alarm signal and provides an indication of the condition of excess allergen particulates present in the environment.

The invention may further include the controller means for further generating, for a predetermined period of time after the flow control signal is generated, a purge signal. The flow means is responsive to the purge signal for creating air flow in a second direction in the passageway opposite the first direction. The invention may yet further include a flow sensor means disposed in the passageway for detecting the rate of air flow in the passageway and providing a corresponding flow rate signal. The controller means is coupled to the flow sensor and is responsive to the flow rate signal for generating a low flow signal when the flow rate signal reaches a predetermined level indicative of a condition of low air flow through the passageway. The indicator means may also be disposed in the housing and coupled to the controller means for receiving the low flow signal and providing an indication of the low air flow condition. The controller means may also be further responsive to the flow rate signal for modifying the flow control signal. The flow means may be responsive to the modified flow control signal for maintaining a constant air flow through the passageway.

The present invention also envisions a method for providing real time detection of excessive allergens in the environmental air. This method comprises the steps of sampling a quantity of air at predetermined time intervals; filtering particles larger than allergen particle-sized particles from the air sample, detecting in the air sample the presence of allergen sized particles, and providing an indication when the detected level of particles in the air sample exceeds a predetermined level.

BRIEF DESCRIPTION OF THE DRAWINGS

The features, objects and advantages of the present invention will become more apparent from the detailed description of the preferred embodiments of the present invention in which like reference characters correspond throughout and wherein.

DETAILED DESCRIPTION OF THE PREFERRED EMBODIMENTS

Figure 1:
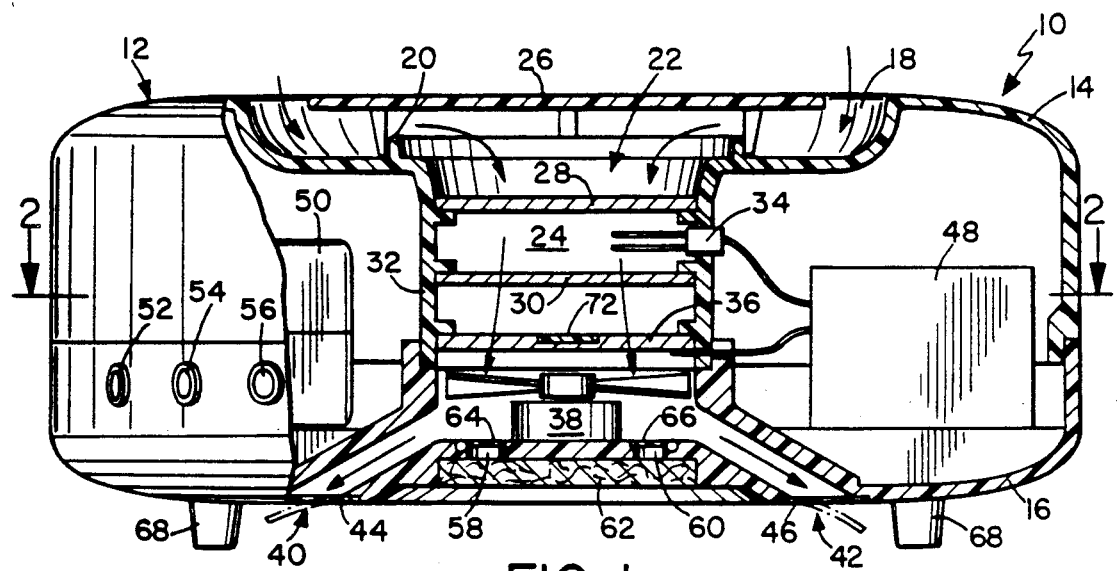
FIG. 1 is a side elevation view of the allergen detector of the present invention with portions cut away and air flow during sampling.

Turning now to FIG. 1, there is shown a selfcontained, real-time allergen detector and warning device 10 which includes a housing 12 formed from a top portion 14 and a bottom portion 16. Although housing 12 is illustrated in FIG. 1 as being cylindrical in nature it may also be of various other configurations such as rectangular or square. It is preferable that the housing be small, for example, approximately six inches in diameter and three inches in heighth. Housing 12 is typically formed from a lightweight material such as plastic.

Housing 12 has formed therein a central passageway to permit air flow through the housing. At the center of top portion 14, an annular recessed portion 18 having a raised central annular ridge 20 is formed. Central to ridge 20 is formed an intake opening 22 of passageway 24. Partially covering opening 22 is a protective cover 26. Cover 26 permits air passage in recessed portion 18 to the opening 22. Cover 26 and ridge 20 prevent large particles from falling directly into opening 22.

Opening 22 and passageway 24 are typically circular in nature, however, other shapes may be utilized for the passageway. Mounted at opening 22 is a first filter 28 which is sized to remove visible particles. Mounted midway into passageway 24 is a second filter 30 which is utilized to remove particles passing through filter 28 that are larger than approximately 50 microns in size. Mounted in sidewall 32 of passageway 24 is a thermal flow sensor 34. Sensor 34 extends into passageway 24 between filters 28 and 30. Flow sensor 34 is a well known type flow sensor which is capable of detecting low air flow rates and providing an electrical signal indicative of the air flow rate.

Further disposed in passageway 24 is allergen particulate detector or sensor 36. Sensor 36 is porous to permit air flow passing thereto while trapping particles in the size range of 5 to 50 microns. Sensor 36 is electrically affected by the collection of particles thereupon. Sensor 36 provides an electrical signal indicative of the number of particles in the 5-50 micron range which collect thereupon. Alternatively a small collated light shining on a transparent surface would register the amount of interference with the passage of light by the build-up of particles on the surface by a light sensor underneath.

Also disposed in passageway 24 beneath detector 36 is a reversible fan 38. Fan 38 provides air flow through passageway 24 via opening 20 and exhaust openings 40 and 42. The flow of air through device 10 during an allergen sample period is indicated by the arrows (unnumbered). Mounted at exhaust openings 40 and 42 are respectively flutter or one-way valves 44 and 46. During the allergen sampling period, air flows through the passageway 24 as indicated by the arrows. Valves 44 and 46 open to permit air to exit from passageway 24. In FIG. 1, valves 40 and 46 are illustrated as being closed, with the valves open during air flow being illustrated in dashed lines.

Also mounted within housing 12 is a controller (not shown) which is mounted in controller housing 48. The controller provides electronic control of device 10 including flow and particulate detection; and warning indications. Also mounted within housing 12 is a power source such as batteries (not shown) positioned in battery case 50. Further mounted within case 12, particularly in lower portion 16, are three status indicators 52, 54 and 56, typically LEDs. Indicators 52, 54 and 56 are respectively provide different colored light indication, typically green, yellow and red. A green indication indicates that the device is operational. A yellow indication indicates the presence of excessive allergens in the environment. A red indication indicates service is required. For purposes of illustration, the wiring other than between sensor 34 and the controller along with the wiring between detector 36 and the controller is omitted.

Housing 12 also includes at the end opposite opening 22, purge openings 58 and 60. Purge openings 58 and 60 intersect passageway 24 beneath fan 38. Filter 62, typically of the well-known HEPA type, is mounted in housing lower portion 16 overlying purge openings 58 and 60. Mounted interior of passageway 24 and overlying purge openings 58 and 60 respectively are flutter or one way valves 64 and 66. Valves 64 and 66 open inwardly towards the passageway 24. The operation of valves 64 and 66 will be described later during the purge operation described with reference to FIG. 3.

Housing 12 also includes extending downwardly from bottom portion 16, feet 68 which are used to support device 10 when placed upon a substantially horizontal surface. Feet 68 also provide spacing from the surface upon which device 10 is placed and exhaust openings 40 and 42. In the alternative, device 10 may be mounted by bracket 70 (FIG. 2) upon a wall or on other vertical surfaces.

Figure 2:
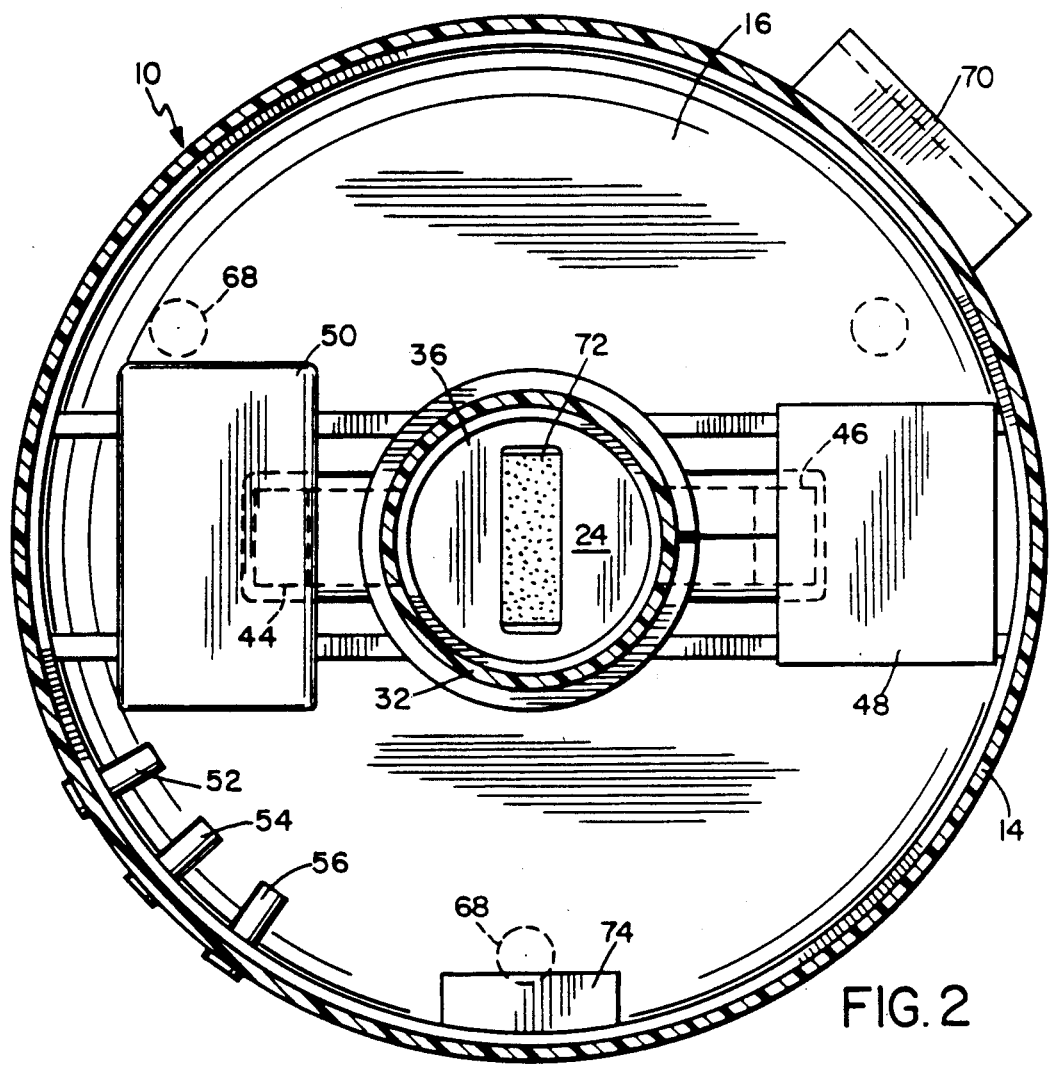
FIG. 2 is a sectional view taken on line 2—2 of FIG. 1.

FIG. 2 illustrates a top view taken along line 2—2 of FIG. 1 and further illustrates the interior components of device 10. In FIG. 2, controller housing 48 and battery case 50 are disposed in a cavity formed within housing 12 exterior to passageway 24. Detector 36 has mounted in a central portion thereof a rectangular piece of material or "sticky" slide 72 which traps allergen particulates thereupon. Slide 72 may be removed for later evaluation of the type of allergen particles collected thereupon. FIG. 2 also illustrates mounted in housing 12 annunciator 74 which provides an audible indication, such as a beeping-sound. Annunciator 74 is driven by the controller to provide an audible indication during and/or after the sample period when an excessive allergen particulate level is detected.

Figure 3:
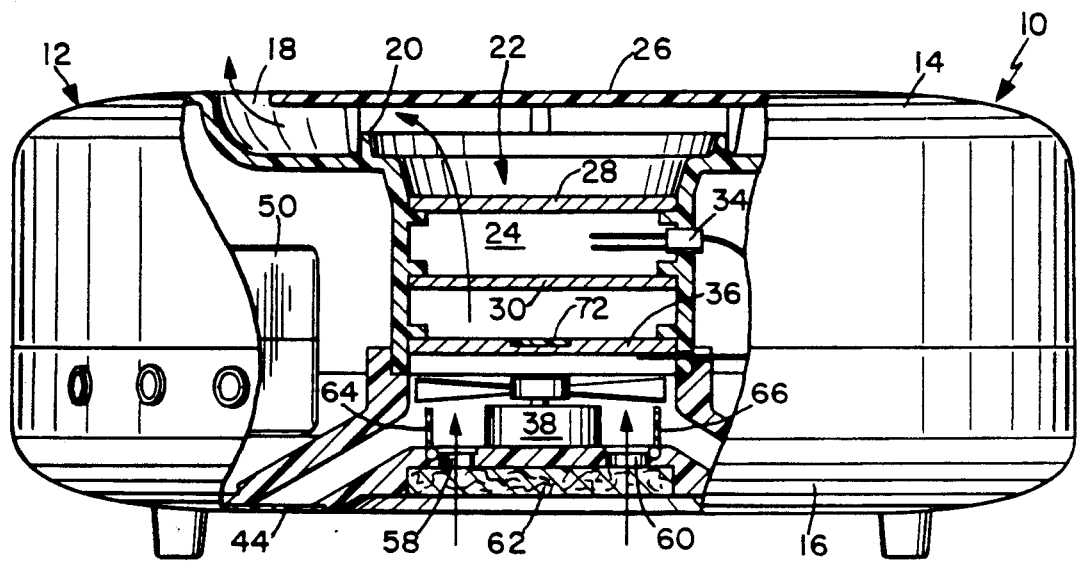
FIG. 3 is a view similar to FIG. 1 showing the purging action.
Figure 4:
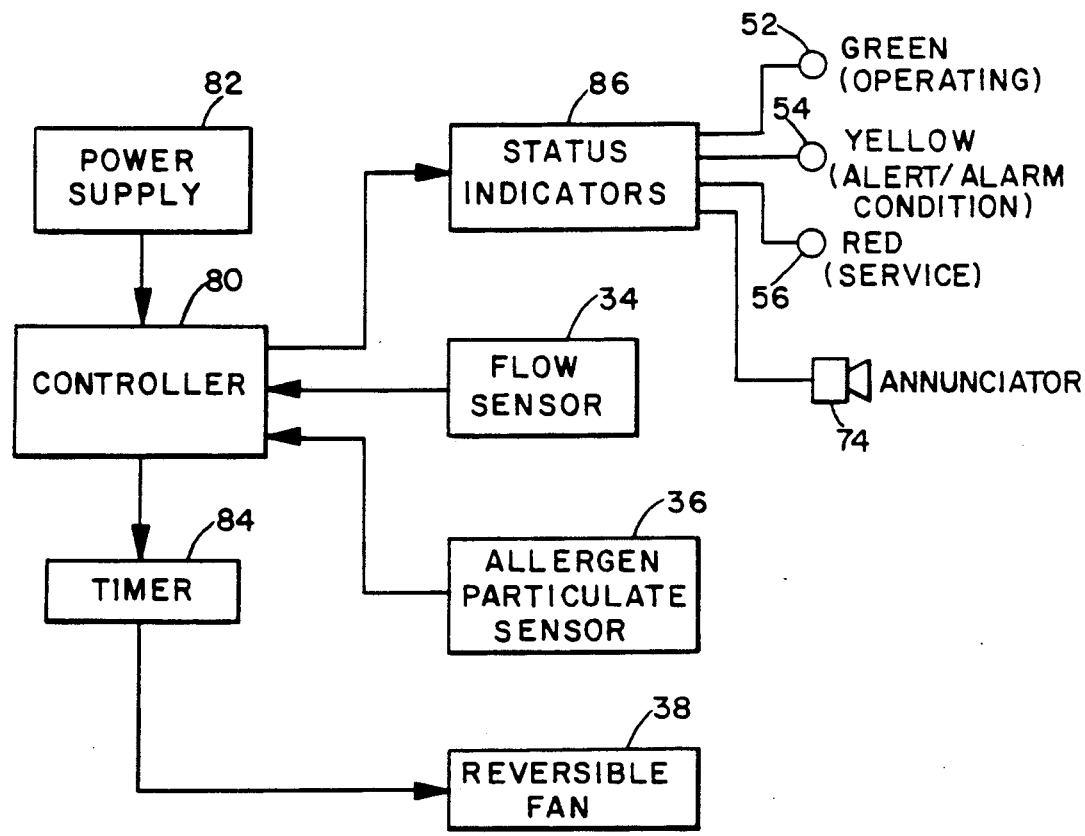
FIG. 4 is a block diagram of the control system.

FIG. 1 illustrates the operation of the device 10 during a sampling mode while FIG. 3 illustrates the operation of the device during a purge mode. FIG. 4 illustrates in block diagram form the electronic controlling circuitry of device 10.

In FIG. 4, controller 80 is mounted within controller housing 48 and receives power from batteries or power supply 82 positioned within battery case 50. Controller 80 is also coupled to timer 84 which may be integrally formed in controller 80 or a separate timing element. Controller 80 is programmed to initiate periodically, such as once every ten minutes or at greater or lesser time periods, the sampling of the environment for allergen particulates. Controller 80 provides a control signal to timer 84 which activates or "turns on" reversible fan 38 to provide flow in passageway 24 (FIG. 1). Fan 38 causes an air flow through the filters 28 and 30, and sensor 36 for a predetermined period of time. Flow sensor 34 monitors the flow rate such that controller 80 may adjust the time period that the fan is "on" or the speed of the fan to respectively maintain either a predetermined air sample quantity that has flowed through the passageway or a constant flow through the passageway. During a sample period air flows through the passageway, such as indicated by the arrows in FIG. 1 in passageway 24. Sensor 36 provides an electrical signal corresponding to the amount of particles that collect upon the sensor during the sample period.

Status indicators, generally indicated by the block 86, are used to provide visual and audible indication of certain conditions. Status indicators 86 or controller 82 may include the necessary LED or annunciator driver circuitry that is well known in the art. Device 10 is in an operational condition when adequate power is provided to the controller 80. Controller 80 thus provides a status indicator via status indicators 86 for, illumination of green LED 52. Illumination of green LED 52 provides a visual indication that the device is "turned on". During the sample period, controller 80 responds to the output of sensor 36 and flow sensor 34 to provide an alert/alarm condition indication when the number of particulates detected by sensor 36, along with the value of air flow during the sample period, indicate that a greater than a predetermined number of particles per cubic meter are present in the environment based upon the air sampled during the sampling period. Controller 80 typically provides constant air flow by adjusting the speed of 38 fan according to the amount of air flow detected by flow sensor 34. Preferably it is the air flow which is adjusted during the sampling period to ensure constant air inflow to compensate for the state of occlusion of the filters. Should sensor 30 detect a condition of allergens exceeding a certain level in the environment, as determined by the measured level of allergen in the sample period, controller 80 provides a signal to status indicators 86 resulting in the illumination of yellow LED 54. Status indicator 84 also drives annunciator 74 to provide an audible indication of the alert/alarm condition.

In the event that occlusion of the filters has occurred sufficient that fan 38 is unable to compensate for the occlusion and maintain a constant flow, controller 80 will provide a signal to status indicators 86 resulting in the illumination of the red LED 56. Such an indication would mean that operator assistance would be required to place the device back in condition for operation. This condition may be alleviated by removal and cleaning of the filters or a purge condition be necessary to place the device back in operation. Also such an indication should be interpreted that an alert/alarm condition may be invalid.

Although not illustrated in FIG. 4, the device 10 may also include provisions for initiating a manual purge input at controller 80. Furthermore an "on-off" switch may be provided between power supply 82 and controller 80 to enable/disable the device operation.

At the end of a sample period, controller 80 instructs, via timer 30, fan 38 to reverse direction. Reversal of fan 38 provides a reversed air flow through passageway 24 as illustrated in FIG. 3 by the unmarked arrows in passageway 24. Reversing direction of the fan 38 results in a reversed air flow from that of FIG. 1, such that valves 44 and 46 close thereby creating a vacuum about fan 38. Upon the vacuum reaching a certain level within passageway 24, valves 64 and 66 open with a "puff" of air entering through filter 62 and openings 58 and 60 into passageway 24. The "puff" of air is utilized to "blow back" particles trapped in sensor 36, filter 30 and filter 28, out through opening 22. At the end of purge cycle, controller 80, via timer 84, turns "off" fan 38 with valves 64 and 66 closing as a result of the loss of air flow. Device 10 is thus put in an idle state until another sampling cycle is to begin.

It is envisioned that the device of the present invention will be set for a predetermined flow rate, sample period and frequency of sampling. Furthermore, each sampling period would be followed by a purge cycle whose period of time would be also determined in the overall operation of the device. It is preferred that the device be either attached to a wall or ceiling or free standing on a table or bookcase. The device should not be placed on a floor because of possible misleading indications obtained in the floor area. Ideal placement of the device 10 would be at face level when sitting to standing, i.e. or approximately 4-6 feet above the floor.

The previous description of the preferred embodiment is provided to enable any person skilled in the art to make or use the present invention. Various modifications to these embodiments will be readily apparent to those skilled in the art, and the generic principles defined herein may be applied to other embodiments without the use of the inventive faculty. Thus, the present invention is not intended to be limited to the embodiments shown herein, but is to be accorded the widest scope consistent with the principles and novel features disclosed herein.

I claim:

1. Apparatus for sampling environmental air for allergen particulates and providing an alarm indication when said allergen particulates exceed a predetermined level, comprising:

a housing having first and second openings at opposite sides of said housing and a passageway formed in said housing between said openings with said passageway defining a direct airflow duct;

flow means disposed in said passageway and responsive to a flow control signal for creating air flow in a first direction through said passageway with air entering said passageway through said first opening and exiting said passageway through said second opening;

filter means disposed in said passageway for removing particulates larger then allergen particulates in air flowing through said passageway in said first direction;

allergen particulate detector means disposed in said passageway downstream of said filter means with respect to said first direction for detecting allergen particulates, in the size range of 5-50 microns, in air flowing in said first direction through said passageway with said air flow created by said flow means, and for providing a detection signal corresponding to the level of allergen particulates present in said air flow;

controller means disposed in said housing and coupled to said flow means and said detector means for, at periodic time intervals, generating for a predetermined time period said flow control signal, and responsive to said detection signal for generating an alarm signal when said detection signal reaches a predetermined level corresponding to the presence of excessive allergen particulates in said air flowing in said first direction in said passageway and further indicative of a condition of excessive allergen particulates present in said environment air; and alarm indicator means, disposed in said housing and coupled to said controller means for receiving said alarm signal and providing an indication of said condition of excessive allergen particulates present in environment.

2. The allergen detector of claim 1 wherein said alarm indicator means provides a visual indication of said condition.

3. The allergen detector of claim 1 wherein said alarm indicator means provides an audible indication of said condition.

4. The allergen detector of claim 2 wherein said alarm indicator means provides an audible indication of said condition.

5. The allergen detector of claim 1 wherein said controller means further generates, for a predetermined period of time after said flow control signal, a purge signal, said flow means responsive to said purge signal for creating air flow in a second direction through said passageway opposite said first direction with air entering said passageway through said second opening and exiting said passageway through said first opening.

6. The allergen detector of claim 5 further comprising purge filter means disposed in said passageway at said second opening for filtering air entering said passageway in said second direction.

7. The allergen detector of claim 1 further comprising:

flow sensor means disposed in said passageway for detecting the rate of air flow in said passageway and providing a corresponding flow rate signal, said controller means responsive to said flow rate signal for generating a low flow signal when said flow rate signal reaches a predetermined level indicative of a condition of low air flow through said passageway; and flow indicator means disposed in said housing and coupled to said controller means for receiving said low flow signal and providing visual indication of said low air flow condition.

8. The allergen detector of claim 7 wherein said controller means is further responsive to said flow rate signal for modifying said flow control signal, said flow means responsive to said modified flow control signal for maintaining constant air flow in said passageway.

9. The allergen detector of claim 1 wherein said allergen particulate detector means further comprises removable specimen means for trapping and retaining allergen particles.

10. A self-contained allergen detector, comprising:

a housing having a passageway formed therethrough with an intake opening formed at one end of said passageway, at least one exhaust opening formed at another end of said passageway, and at least purge opening formed at said passageway other end;

flow means disposed in said passageway adjacent said passageway other end and responsive to a flow control signal and a purge signal for respectively creating air flow through said passageway in first and second direction, said first direction from said intake opening to said exhaust opening and said second direction from said purge opening to said intake opening;

first filter means disposed in said passageway adjacent said intake opening for removing visible sized airborne particles in air flowing in said passageway in said first direction;

second filter means disposed in said passageway between said first filter means and said flow means for removing airborne particles in the range smaller than visible sized particles to larger than fifty microns in air flowing in said passageway in said first direction;

third filter means disposed at said exhaust opening for removing airborne particles in air flowing in said passageway in said second direction;

detector means disposed in said passageway between said second filter means and said flow means for detecting the presence of airborne particles in the size range of approximately 5 to 50 microns in air flowing in said passageway in said first direction and providing a corresponding detection signal;

flow sensor means disposed in said passageway between said first and second filters for detecting the level of air flow in said passageway and providing a corresponding flow rate signal;

controller means disposed in said housing and coupled to said flow means, said detector means and said flow sensor means, for generating said flow control signal during a sample period for receiving said detection signal and said flow signal during said sample period, for generating an alarm signal when said detection signal is indicative of a condition of an excess of a predetermined quantity of particles in air flow in said first direction during a sample period, for generating a low flow signal when said flow rate signal is indicative of air flow lower than a predetermined level during said sample period, said controller means further responsive to said flow rate signal for modifying said flow control signal, said flow means responsive to said modified flow control signal for maintaining constant air flow in said passageway during said sample period, and said controller means further for generating said purge signal during a purge period following said sample period; and indicator means, coupled to said controller means, responsive to said alarm signal for generating at least one of a visual indication and an audible indication of said excessive particle condition, and for responsive to said low flow signal and providing visual indication of low air flow during said sample period.

11. The detector of claim 10 further comprising power source means disposed in said housing for providing electrical power to said flow means, said detector means, said flow sensor means and said controller means.

12. The detector of claim 11 wherein said flow means comprises:

a reversible fan mounted within said housing;

a first one way valve mounted at each exhaust opening, each first valve opening outwardly from said passageway; and a second one way valve mounted at each purge opening, each second valve opening inwardly towards said passageway.

13. The detector of claim 10 further comprising trap means disposed upon said detector means for trapping particulates passing through said first and second filter means to said detector means.

14. An allergen detector for sampling the environment and providing an alarm indication when allergen particulates exceed a predetermined level, said detector comprising:

a housing having a passageway formed therethrough;

flow means disposed in said passageway and responsive to a flow control signal for creating air flow in a first direction through said passageway;

filter means disposed in said passageway for removing particulates larger than allergen particulates in air flowing through said passageway in said first direction;

allergen particulate detector means disposed in said passageway downstream of said filter means with respect to said first direction for detecting allergen particulates in air flowing through said passageway and for providing a corresponding detection signal;

controller means disposed in said housing and coupled to said flow means and said allergen detector means for, at periodic time intervals, generating for a predetermined time period said flow control signal, and responsive to said detection signal for generating an alarm signal when said detection signal reaches a predetermined level indicative of a condition of excessive allergen particulates present in the environment;

alarm indicator means, disposed in said housing and coupled to said controller means for receiving said alarm signal and providing an indication of said condition of excessive allergen particulates present in the environment;

flow sensor means disposed in said passageway for detecting the rate of air flow in said passageway and providing a corresponding flow rate signal, said controller means responsive to said flow rate signal for generating a low flow signal when said flow rate signal reaches a predetermined level indicative of a condition of low air flow through said passageway; and flow indicator means disposed in said housing and coupled to said controller means for receiving said low flow signal and providing visual indication of said low air flow condition.

15. The allergen detector of claim 14 wherein said controller means is further responsive to said flow rate signal for modifying said flow control signal, said flow means responsive to said modified flow control signal for maintaining constant air flow in said passageway.

16. An allergen detector for sampling the environment and providing an alarm indication when allergen particulates exceed a predetermined level, comprising:

a housing having a passageway formed therethrough;

flow means disposed in said passageway and responsive to a flow control signal for creating air flow in a first direction through said passageway;

filter means disposed in said passageway for removing particulates larger than allergen particulates in air flowing through said passageway in said first direction;

allergen particulate detector means disposed in said passageway downstream of said filter means with respect to said first direction for detecting allergen particulates in air flowing trough said passageway and for providing a corresponding detection signal;

specimen means for removably disposed in said passageway downstream of said filter means with respect to said first direction for trapping and retaining allergen particles;

controller means disposed in said housing and coupled to said flow means and said allergen detector means for, at periodic time intervals, generating for a predetermined time periodic said flow control signal, and responsive to said detection signal for generating an alarm signal when said detection signal reaches a predetermined level indicative of a condition of excessive allergen particulates present in the environment; and alarm indicator means, disposed in said housing and coupled to said controller means for receiving said alarm signal and providing an indication of said condition of excessive allergen particulates present in the environment.

17. The allergen detector of claim 16 wherein said specimen means is disposed in said passageway downstream, with respect to said first direction, of said particulate detector means.

18. The allergen detector of claim 17 wherein said specimen means comprises an allergen particulate collecting slide removably mounted within said passageway.

19. A method for providing real-time detection of excessive allergens in the environmental air comprising the steps of:

sampling a quantity of air at predetermined time intervals;

filtering particles larger than allergen particle-size particles from said air sample;

detecting in said air sample the presence of allergen-sized particles;

providing a first indication when said detected particles in said air sample exceed a predetermined level;

detecting the rate of air flow in said air sampling; and providing a second indication when said air flow is below a predetermined level indicative of insufficient air in said air sample.

20. The method of claim 19 further comprising the step of purging, at times other than during said sampling, in said air sample, said particles larger than allergen-size particles from a filter provided for filtering said larger than allergen-size particles in said air sample.

* * * * *